US006080573A

United States Patent [19]

Convents et al.

[11] Patent Number: 6,080,573

[45] Date of Patent: Jun. 27, 2000

[54] ENZYMATIC OXIDATION PROCESS

[75] Inventors: Daniel Convents, Merelbeke, Belgium; Rudolf Willem Pieter van Drunen, Maassluis; Cornelis Theodorus Verrips, Vlaardingen, both of Netherlands

[73] Assignee: Lever Brothers Company, Division of Conopco, Inc., New York, N.Y.

[21] Appl. No.: 08/977,586

[22] Filed: Nov. 25, 1997

[30] Foreign Application Priority Data

Nov. 25, 1996 [EP] European Pat. Off. .............. 96203305

[51] Int. Cl.[7] .............................. C11D 3/386; C12P 1/00; C12N 9/08; D06M 16/00

[52] U.S. Cl. ............................ 435/263; 435/41; 435/192; 435/264; 510/530

[58] Field of Search .............................. 435/192, 41, 264, 435/263; 510/530

[56] References Cited

U.S. PATENT DOCUMENTS

| | | | |
|---|---|---|---|
| 5,700,769 | 12/1997 | Schneider et al. ...................... | 435/192 |

FOREIGN PATENT DOCUMENTS

| | | |
|---|---|---|
| 086139 | 8/1983 | European Pat. Off. . |
| 189687 | 8/1986 | European Pat. Off. . |
| 266348 | 3/1992 | France . |
| 1944904 | 4/1971 | Germany . |
| 282-588 | 12/1927 | United Kingdom . |
| 91/05839 | of 0000 | WIPO . |
| 94/12620 | of 0000 | WIPO . |
| 91/05839 | 5/1991 | WIPO . |
| 92/18683 | 10/1993 | WIPO . |
| 94/12619 | 6/1994 | WIPO . |
| 94/12620 | 6/1994 | WIPO . |
| 94/12621 | 6/1994 | WIPO . |
| 95/01426 | 1/1995 | WIPO . |
| 95/07988 | 3/1995 | WIPO . |
| 96/10079 | 4/1996 | WIPO . |
| 96/06930 | 7/1996 | WIPO . |
| 97/31090 | 8/1997 | WIPO . |

*Primary Examiner*—Herbert J. Lilling

[57] ABSTRACT

There is provided an enzymatic oxidation process wherein a substance which is to be oxidised is reacted with (a) an enzyme exhibiting peroxidase activity and a source of hydrogen peroxide or an enzyme exhibiting oxidase activity on phenolic compounds and (b) a compound which enhances the oxidation activity of the enzyme, characterized in that the compound specifically binds the substance which is to be oxidized. Furthermore, there is provided an enzymatic stain bleaching or anti dye-transfer composition comprising: (a) an enzyme exhibiting peroxidase activity and a source of hydrogen peroxide or an enzyme exhibiting oxidase activity on phenolic compounds and (b) a compound which enhances the oxidation activity of the enzyme and which is capable of binding selectively to a stain chromophore or textile dye in solution.

5 Claims, No Drawings

ENZYMATIC OXIDATION PROCESS

TECHNICAL FIELD

The present invention generally relates to an enzymatic oxidation process wherein a substance which is to be oxidised is reacted with a laccase, or with a peroxidase and a source of hydrogen peroxide, in the presence of a compound which enhances the oxidation reaction. More in particular, the invention relates to an enzymatic detergent composition for stain bleaching or anti dye-transfer.

BACKGROUND AND PRIOR ART

Peroxidases and laccases are well described as enzymes which can be used to catalyse the oxidation reaction of a substrate with hydrogen peroxide or molecular oxygen, respectively. Several applications of these enzymes in oxidative processes have been described. Such applications include, amongst others, stain bleaching and anti dye-transfer in detergents, polymerization of lignin, in-situ depolymerization of lignin in Kraft pulp, bleaching of denim dyed garments, polymerization of phenolic substances in juices and beverages and hair bleaching (WO-A-92/18683, WO-A-95/07988, WO-A-95/01426).

WO-A-91/05839 (Novo Nordisk) discloses enzymatic anti dye-transfer compositions comprising an (a) an enzyme exhibiting peroxidase activity and a source of hydrogen peroxide or (b) an enzyme exhibiting oxidase activity on phenolic compounds. The compositions are said to bleach any dissolved dye so that no dye can redeposit upon the fabric.

Characteristic to peroxidases and laccases is that they have little substrate specificity. Most small phenolic molecules are substrates to these enzymes. The range of molecules which can be oxidized by these enzymes can be extended by the addition of so-called enhancers. These molecules are then the primary substrate for the enzymes. Upon reaction with the enzyme, the enhancers are oxidized to generate radicals which subsequently oxidize the final substrate of interest.

Several classes of molecules have been described as enhancers for peroxidases and/or laccases. Among these are simple substituted phenols, benzidine derivatives, phenothiazine derivatives, and azino compounds (WO-A-94/12619, WO-A-94/12620 and WO-A-94/12621, all Novo Nordisk). The value of these enhancers has been demonstrated in anti dye transfer compositions for detergents.

Whereas enhancers broaden the range of substrates which can be oxidized by the enzyme, they do not incorporate any substrate specificity in the oxidation process. To the contrary, addition of enhancers renders the oxidation reaction more aggressive and difficult to control.

We have now surprisingly found that it is possible to control the enzymatic oxidation reaction by incorporating substrate selectivity into the enhancer molecule. The addition of a selective enhancer was found to allow the tailoring of the otherwise largely random oxidation process.

Moreover, we have identified an experimental procedure which allows the development of such selective enhancers. We have found that peptides, which selectively bind the substrate to be oxidized by a peroxidase or a laccase, can act as such an enhancer. Therefore, for the identification of selective enhancers, one needs to screen for peptides which bind to the molecule to be oxidized, and then from those binding peptides, screen and/or develop a peroxidase/laccase enhancer.

The use of peroxidases and laccases with enhancers has so far most extensively been described in the areas of pharmaceutical kits and detergent anti dye-transfer compositions. Especially in the latter application, incorporation of selectivity in the bleach reaction is of high value. For dye-transfer prevention, the dye should only be bleached in solution, without causing dye damage to the fabric. Stain bleaching compositions should be targeted towards oxidation of the stain chromophores, as opposed to the dye molecules on the garments.

DEFINITION OF THE INVENTION

According to a first aspect of the invention, there is provided an enzymatic oxidation process wherein a substance which is to be oxidised is reacted with (a) an enzyme exhibiting peroxidase activity and a source of hydrogen peroxide or an enzyme exhibiting oxidase activity on phenolic compounds and (b) a compound which enhances the oxidation activity of the enzyme, characterized in that the compound selectively binds the substance which is to be oxidized.

According to a second aspect, there is provided an enzymatic stain bleaching or anti dye-transfer composition comprising: (a) an enzyme exhibiting peroxidase activity and a source of hydrogen peroxide or an enzyme exhibiting oxidase activity on phenolic compounds and (b) a compound which is capable of binding selectively to a stain chromophore or textile dye in solution.

DESCRIPTION OF THE INVENTION

In a first aspect, the invention relates to an enzymatic oxidation process wherein a substance which is to be oxidised is reacted with (a) an enzyme exhibiting peroxidase activity an a source of hydrogen peroxide or an enzyme exhibiting oxidase activity on phenolic compounds and (b) a compound which enhances the oxidation activity of the enzyme. According to the invention, the compound which enhances the oxidation reaction is capable of binding selectively to the substance which is to be oxidised. The oxidation process can be used within a detergent composition, specifically suited for stain bleaching and/or dye transfer prevention purposes, and this constitutes a second aspect of the invention. The detergent composition may take any suitable physical form, such as a powder, an aqueous or non aqueous liquid, a paste or a gel.

(a) The enzyme

The enzymatic oxidation composition according to the invention comprises, as a first constituent, an enzyme. The enzyme may either be an enzyme exhibiting peroxidase activity (which is then used together with a source of hydrogen peroxyde), or an enzyme exhibiting oxidase activity on phenolic compounds, such as phenol oxidase or laccase. Suitable enzymes are disclosed in EP-A-495 835 (Novo Nordisk). For instance, suitable peroxidases may be isolated from and are producible by plants or microorganisms such as bacteria or fungi. Preferred fungi are strains belonging to the class of the *Basidiomycetes,* in particular *Coprinus,* or to the class of *Hyphomycetes,* in particular *Arthromyces,* especially *Arthromyces ramosus.* Other preferred sources are *Hormographiella* sp., *Myxococcus* sp., *Corallococcus* sp. (WO-A-95/11964), or Soybean peroxidase. Examples of suitable enzymes exhibiting oxidase activity on phenolic compounds are catechol oxidase and laccase and bilirubin oxidase. The laccase can be derived from fungi such as *Trametes* sp., *Collybio* sp., *Fomes* sp., *Lentinus* sp., *Pleurotus* sp., *Rhizoctonia* sp., *Aspergillus* sp.,

*Neurospora* sp., *Podospora* sp., *Phlebia* sp., *Coriolus* sp., *Myceliophthora* sp., *Coprinus* sp., *Panaeolus* sp., *Psathyrella* sp. (WO-A-96/06930). Bilirubin oxidase can be obtained from *Myrothecium* sp. or *Stachibotrys* sp.

The enzymatic oxidation compositions of the invention comprise about 0.001 to 10 milligrams of active enzyme per litre. A detergent composition will comprise about 0.001% to 1% of active enzyme (w/w). The enzyme activity can be expressed as ABTS (2,2'-azino-bis(3-ethylbenzothiazoline-6-sulphonic acid) units. One ABTS unit represents the amount of enzyme which oxidizes ABTS, resulting in an increase of 1 optical density at 418 nm in one minute. Conditions for the activity assay are 2 mM ABTS, 1 mM $H_2O_2$, 20 mM Tris, pH 9. The enzyme activity which is added to the enzymatic oxidation composition will be about 10 to $10^6$ ABTS units per litre, preferably $10^3$ to $10^5$ ABTS units per litre.

The enzymes used in the present invention can usefully be added to the detergent composition in any suitable form, i.e. the form of a granular composition, a liquid or a slurry of the enzyme, or with carrier material (e.g. as in EP-A-258 068 and the Savinase (TM) and Lipolase (TM) products of Novo Nordisk). A good way of adding the enzyme to a liquid detergent product is in the form of a slurry containing 0.5 to 50% by weight of the enzyme in a ethoxylated alcohol nonionic surfactant, such as described in EP-A-450 702 (Unilever).

(b) The source of hydrogen peroxide

Another ingredient of the enzymatic anti dye-transfer compositions according to the invention is a source of hydrogen peroxide. This may be hydrogen peroxide itself, but more stabilized forms of hydrogen peroxide such as perborate or percarbonate are preferred. Especially preferred is sodium percarbonate.

Alternatively, one may employ an enzymatic hydrogen peroxide-generating system. The enzymatic hydrogen peroxide-generating system may in principle be chosen from the various enzymatic hydrogen peroxide-generating systems which have been disclosed in the art. For example, one may use an amine oxidase and an amine, an amino acid oxidase and an amino acid, cholesterol oxidase and cholesterol, uric acid oxidase and uric acid or a xanthine oxidase with xanthine. Preferably, however, the combination of a $C_1$–$C_4$ alkanol oxidase and a $C_1$–$C_4$ alkanol is used, and especially preferred is the combination of methanol oxidase and ethanol. The methanol oxidase is preferably isolated from a catalase-negative Hansenula polymorpha strain. (see for example EP-A-244 920 (Unilever)).

c. The enhancer

The novel oxidation process according to the present invention is based on the presence of a compound, the peroxidase or oxidase enhancer, which should be capable of binding selectively to the substance which is to be oxidised. The enzymatic oxidation composition will comprise about 0.001 to 10 mg per litre.

The degree of binding of a compound A to another molecule B can be generally expressed by the chemical equilibrium constant $K_d$ resulting form the following binding reaction:

$$[A]+[B]=[A::B]$$

The chemical equilibrium constant $K_d$ is then given by:

$$K_d = \frac{[A]\times[B]}{[A::B]}$$

Whether the binding to the substance is specific or not can be judged from the difference between the binding ($K_d$ value) of the compound to that substance, versus the binding to the material to which that substance is applied, or versus other substances one does not want to oxidize. For substances which occur in stains, the latter material can be envisioned to be the fabric on which the stain is present, or the dye molecules on coloured garments. The difference between the two binding constants should be minimally 100, and preferably more that 1000. Typically, the compound should bind the coloured substance with a $K_d$ value of $1*10^{-4}$ to $1*10^{-6}$, with a background binding to fabric with a $K_d$ of $1*10^{-2}$ to $1*10^{-3}$. Higher binding affinities ($k_d$ of less than $1*10^{-5}$) and/or a larger difference between coloured substance and background binding would increase the selectivity of the oxidation process. Also, the weight efficiency of the compound in the total detergent composition would be increased and smaller amounts of the compound would be required.

Several classes of compounds can be envisaged which deliver the capability of specific binding to substances one would like to oxidize. In the following we will give a number of examples of such compounds having such capabilities, without pretending to be exhaustive.

Antibodies

Antibodies are well known examples of compounds which are capable of binding specifically to compounds against which they were raised. Antibodies can be derived from several sources. From mice, monoclonal antibodies can be obtained which possess very high binding affinities. From such antibodies, Fab, Fv or scFv fragments, can be prepared which have retained their binding properties. Such antibodies or fragments can be produced through recombinant DNA technology by microbial fermentation. Well known production hosts for antibodies and their fragments are yeast, moulds or bacteria. A class of antibodies of particular interest is formed by the Heavy Chain antibodies as found in Camelidae, like the camel or the llama. The binding domains of these antibodies consist of a single polypeptide fragment, namely the variable region of the heavy chain polypeptide (HC-V). In contrast, in the classic antibodies (murine, human, etc.), the binding domain consist of two polypeptide chains (the variable regions of the heavy chain (Vh) and the light chain (V1)). Procedures to obtain heavy chain immunoglobulins from Camelidae, or (functionalized) fragments thereof, have been described in WO-A-94/04678 (Casterman and Hamers) and WO-A-94/25591 (Unilever and Free University of Brussels).

Alternatively, binding domains can be obtained from the Vh fragments of classical antibodies by a procedure termed 'camelization'. Hereby the classical Vh fragment is transformed, by substitution of a number of amino acids, into a HC-V-like fragment, whereby its binding properties are retained. This procedure has been described by Riechmann et al. in a number of publications (J. Mol. Biol. (1996), 259, 5, 957–69; Protein. Eng. (1996), 9, 6, 531–37, Bio/Technology, (1995) 13, 5, 475–79). Also HC-V fragments can be produced through recombinant DNA technology in a number of microbial hosts (bacterial, yeast, mould), as described in WO-A-94/29457 (Unilever).

Peptides

Peptides usually have lower binding affinities to the substances of interest than antibodies. Nevertheless, the experiments described in the examples show that the binding properties of peptides can be sufficient to deliver the desired selectivity in a oxidation process. A peptide which is capable of binding selectively to a substance which one would like to oxidize, can for instance be obtained from a protein which is known to bind to that specific substance. An example of such a peptide would be a binding region extracted from an antibody raised against that substance.

Alternatively, peptides which bind to such substance can be obtained by the use of peptide combinatorial libraries. Such a library may contain up to $10^{10}$ peptides, from which the peptide with the desired binding properties can be isolated. (R. A. Houghten, Trends in Genetics, Vol 9, no &, 235–239). Several embodiments have been described for this procedure (J. Scott et al., Science (1990), Vol. 249, 386–390; Fodor et al., Science (1991), Vol. 251, 767–773; K. Lam et al., Nature (1991) Vol. 354, 82–84; R. A. Houghten et al., Nature (1991) Vol. 354, 84–86).

Suitable peptides can be produced by organic synthesis, using for example the Merrifield procedure (Merrifield, J.Am.Chem.Soc. (1963), 85, 2149–2154). Alternatively, the peptides can be produced by recombinant DNA technology in microbial hosts (yeast, moulds, bacteria) (K. N. Faber et al., Appl. Microbiol. Biotechnol. (1996) 45, 72–79).

Pepidomimics

In order to improve the stability and/or binding properties of a peptide, the molecule can be modified by the incorporation of non-natural amino acids and/or non-natural chemical linkages between the amino acids. Such molecules are called peptidomimics (H. U. Saragovi et al. Bio/Technology (1992), Vol 10, 773–778; S. Chen et al., Proc.Natl.Acad. Sci. USA (1992) Vol. 89, 5872–5876). The production of such compounds is restricted to chemical synthesis.

Other Organic Molecules

It can be readily envisaged that other molecular structures, which need not be related to proteins, peptides or derivatives thereof, can be found which bind selectively to substances one would like to oxidize with the desired binding properties. For example, certain polymeric RNA molecules which have been shown to bind small synthetic dye molecules (A. Ellington et al., Nature (1990) vol. 346, 818–822). Such binding compounds can be obtained by the combinatorial approach, as described for peptides (L. B. McGown et al., Analytical Chemistry, Nov. 1, 1995, 663A–668A).

This approach can also be applied for purely organic compounds which are not polymeric. Combinatorial procedures for synthesis and selection for the desired binding properties have been described for such compounds (Weber et al., Angew.Chem.Int.Ed.Engl. (1995), 34, 2280–2282; G. Lowe, Chemical Society Reviews (1995) Vol 24, 309–317; L. A. Thompson et al. Chem. Rev. (1996), Vol. 96, 550–600). Once suitable binding compounds have been identified, they can be produced on a larger scale by means of organic synthesis.

Obviously, binding alone of the described compound to a substance one would like to oxidize will not be sufficient to drive the oxidation process. Because enzymes like peroxidases and laccases are known to oxidize substances by a one or two electron oxidation mechanism, the compounds which add selectivity to the oxidation process should be capable to transfer one or two electrons from the substance to the enzyme. The incorporation of electron transfer properties into the binding compound can be achieved by the addition of amino Acids into peptides which are known to be important for those properties, e.g. tyrosine, tryptophan, cysteine, histidine, methionine. For organic compounds, aromatic structures should be incorporated, preferentially with one or more heteroatoms (S, N, O).

Several classes of substances one would like to oxidize can be envisaged: For detergents applications, coloured substances which may occur as stains on fabrics can be a target. Several types or classes of coloured substances which may occur in stains can be envisaged, such as indicated below:

1. Porphyrin Derived Structures

Porphyrin structures, often coordinated to a metal, form one class of coloured substances which occur in stains. Examples are heme or haematin in blood stain, chlorophyll as the green substance in plants, e.g. grass or spinage. Another example of a metal-free substance is bilirubin, a yellow breakdown product of heme.

2. Tannins, Polyphenols

Tannins are polymerised forms of certain classes of polyphenols. Such polyphenols are catechins, leuantocyanins, etc. (P. Ribèreau-Gayon, Plant Phenolics, Ed. Oliver & Boyd, Edinburgh, 1972, pp.169–198). These substances can be conjugated with simple phenols like e.g. gallic acids. These polyphenolic substances occur in tea stains, wine stains, banana stains, peach stains, etc. and are notoriously difficult to remove.

3. Carotenoids (G. E. Bartley et al., The Plant Cell (1995), Vol 7, 1027–1038). Carotenoids are the coloured substances which occur in tomato (lycopene, red), mango (β-carotene, orange-yellow). They occur in food stains (tomato) which are also notoriously difficult to remove, especially on coloured fabrics, when the use of chemical bleaching agents is not advised.

4. Anthocyanins (P. Ribèreau-Gayon, Plant Phenolics, Ed. Oliver & Boyd, Edinburgh, 1972, 135–169). These substance are the highly coloured molecules which occur in many fruits and flowers. Typical examples, relevant for stains, are berries, but also wine. Anthocyanins have a high diversity in glycosidation patterns.

5. Maillard Reaction Products

Upon heating of mixtures of carbohydrate molecules in the presence of protein/peptide structures, a typical yellow/brown coloured substance arises. These substances occur for example in cooking oil and are difficult to remove from fabrics.

6. Dyes in Solution

For the prevention of dye transfer from a coloured piece of fabric to other garments during the wash, it valuable to specifically bleach the dye molecules in the wash solution. Several types of fabric dyes are used, and can therefore be envisaged to be a target for the oxidation process: e.g. sulphur dyes, vat dyes, direct dye, reactive dyes and azoic dyes.

The invention will now be further illustrated in the following, non-limiting Examples.

EXAMPLE 1

Binding Characteristics of Peptides

The specific binding of peptide #1 (NH2-GGSCGYHYQHCGQG-COOH) to the dye Reactive Red 6 was measured (the peptide contains one disuphide bridge through the cysteine residues, sequence of the peptides is given in one letter amino acid codes). The binding was demonstrated by a specially for this purpose developed Enzyme Linked Immunosorbent Assay (ELISA).

For the detection of binding, the enzyme Alkaline Phosphatase (AP, 2.5 mg/ml) was conjugated with the reactive dye Reactive Red 6 (RR6, 1.25 mM), by incubation of the enzyme with the dye during 2 hours, at room temperature in Borate buffer, 0.1 M, 0.15 M NaCl, pH 8.5. The dye thereby becomes covalently linked to the amino groups of the enzyme by its triazine unit. Free dye was separated from the enzyme conjugate by gel filtration (PD-10 column, Pharmacia). Elisa plates (Polysorb, Nunc) were coated overnight with 100 $\mu$l of a 1 mg/ml peptide solution in Phosphate buffer, 150 mM NaCl, pH 7.4 (PBS). The peptide coated ELISA plates were blocked with 2% Bovine Serum Albumin (BSA) in PBS for 1 hour, room temperature. The Alkaline Phosphatase—RR6 conjugate (AP-RR6) was then incubated for 1 hour, room temperature, in incubation buffer (0.2 M Tris, 20 mM NaCl, 1% PEG 6000, 5% BSA). The plates were washed plates 3 times with wash buffer (0.2 M Tris, 60 mM Citrate, 0.1 M NaCl, 0.05% Tween) and 3 times with demineralized water. Bound Alkaline Phosphatase (AP) was then detected by incubation with the substrate p-nitrophenyl-phosphate. After 30 minutes, the optical density at 405 nm was measured with a ELISA plate reader. As a control, Alkaline Phosphatase, not conjugated to the dye, was used. Furthermore, plates were coated with the peptides Arg-Arg, Lys-Lys-Lys and Val-Gly-Ser-Glu, to demonstrate the specificity of the dye binding peptide. The results as optical densities at 405 nm are given in the table below.

| | OD 450 nm values | |
|---|---|---|
| | AP-RR6 | AP |
| Peptide #1 | 2.36 | 0.047 |
| Arg—Arg | 0.09 | 0.003 |
| Lys—Lys—Lys | 0.31 | 0.023 |
| V—G—S—E | 0.03 | 0.003 |

EXAMPLE 2

Binding Characteristics of the Peptide

The binding of peptide #1 was further demonstrated by direct measurement of the binding kinetics of the peptides to the dyes in a IASys Biosensor (Fisons). By means of the reactive triazine group of the dye, reactive red 6 (RR-6) and reactive red 120 (RR-120) were coupled to an aminosilane surface cell of the instrument. Dye solutions were 1 mM in 0.1 M borate buffer, 0.15 NaCl, pH 8.5. The cell was incubated for 2 hours at 37° C. for RR-6 and overnight at 37° C. for RR-120. After coupling the sample cell was extensively washed with PBS, 0.05% Tween. For the measurement of the binding affinity between the peptide and the dye, solutions of increasing concentration of peptide were added to the cuvette, and binding kinetics were monitored. From these kinetics, the binding affinities, as equilibrium dissociation constants, were calculated. The results are shown below. Equilibrium dissociation constants, $K_d$, for the reaction $$[\text{Peptide}]+[\text{Dye}]\rightleftharpoons[\text{Peptide::Dye}]$$

is given by:

$$K_d = \frac{[\text{Peptide}] \times [\text{Dye}]}{[\text{Peptide :: Dye}]}$$

Below are shown the $K_d$ values for the binding of the peptides to the two different dyes.

| | $K_d$ values |
|---|---|
| RR-6 | $1 \cdot 10^{-4}$ |
| RR-120 | $5 \cdot 10^{-5}$ |

EXAMPLE 3

Peroxidase Bleach Enhancement by Peptides

Dye bleach experiments were performed using a partially purified peroxidase derived from an *Hormographiella* species. The enzyme was purified by ultrafiltration from the fermentation broth, followed by ion-exchange chromatography using Q-Sepharose (Pharmacia) at pH 7. Enzyme activity is expressed as ABTS (2,2'-azino-bis(3-ethylbenzothiazoline-6-sulphonic acid) units. One ABTS unit represents the amount of enzyme which oxidizes ABTS, resulting in an increase of 1 optical density at 418 nm. Conditions for the activity assay were 2 mM ABTS, 1 mM $H_2O_2$, 20 mM Tris, pH 9.

Bleaching experiments were conducted at 25° C. in 20 mM Phosphate buffer, set at pH 9. Added peroxidase activity was 60 ABTS units per millilitre. The peptide GGSCGYHYQHCGQG (one letter amino acid code) was added as a peroxidase enhancer at a concentration of 100 $\mu$M. The Reactive Black 5 concentration was 30 $\mu$M, and the $H_2O_2$ concentration was 250 $\mu$M.

Bleaching of Reactive Black 5 was monitored by the decrease in optical density at 590 nm. The enhancing activity of the peptide was compared to that of the free amino acid tyrosine. As the peptide contains 2 tyrosine residues, 200 $\mu$M of the amino acid was added, as a comparison to 100 $\mu$M of peptide. The enhanced bleaching activity at pH 9, 25° C., of the peroxidase in the presence of the peptide can be seen from the table below, which shows the OD reading at 590 nm at the indicate time intervals.

| | Enhancer | | |
|---|---|---|---|
| Minutes after incubation | none | tyrosine 200 $\mu$M | peptide 100 $\mu$M |
| 0 | 0.651 | 0.651 | 0.651 |
| 2 | 0.639 | 0.606 | 0.430 |
| 4 | 0.634 | 0.580 | 0.344 |
| 6 | 0.631 | 0.559 | 0.294 |
| 8 | 0.628 | 0.540 | 0.263 |

-continued

| | Enhancer | | |
|---|---|---|---|
| Minutes after incubation | none | tyrosine 200 μM | peptide 100 μM |
| 10 | 0.625 | 0.523 | 0.241 |
| 12 | 0.623 | 0.507 | 0.227 |
| 14 | 0.620 | 0.494 | 0.216 |

EXAMPLE 4

Bleaching of Red Beet Solution with Peroxidase—Peptide Enhanced Reaction

In order to study the selectivity of the peptide enhanced reaction, the bleaching of a red beet solution with the system was assayed. The extract of red beet is, as with dyes, susceptible the action of peroxidase enhancers. The figure below shows that there is not reaction enhancement of the peptide over tyrosine. Experimental conditions are as in example 3.

| Minutes after | Enhancer | | |
|---|---|---|---|
| incubation | none | tyrosine | peptide |
| 0 | 1.09 | 1.082 | 1.091 |
| 2 | 1.084 | 1.076 | 1.083 |
| 4 | 1.067 | 1.06 | 1.063 |
| 6 | 1.033 | 1.022 | 1.016 |
| 8 | 0.94 | 0.906 | 0.881 |
| 10 | 0.796 | 0.739 | 0.709 |
| 12 | 0.663 | 0.591 | 0.567 |
| 14 | 0.56 | 0.488 | 0.477 |

EXAMPLE 5

Dye Transfer Prevention

The potential of the enzymatic system to prevent dye transfer was assessed by washing a coloured swatch in the presence of a white pick-up swatch. The experiments were performed in 25 ml Phosphate buffer, pH 9, containing the two swatches of 5x5 cm. The experiments were performed using a partially purified peroxidase derived from an *Hormographiella* species. Experiments were performed in the presence of 12 ABTS units/ml. The fabrics were agitated in the wash solution (25 ml) for 30 minutes at 40° C. The fabrics were line dried and the reflectance spectra were measured using a Minolta spectrometer. The data thereby obtained was transferred to the CIELAB L*a*b* colour space parameters. In this colour space, L* indicates lightness and a* and b* are the chromaticity coordinates. The colour differences between the control swatch, without addition the peptide enhancer, and the swatches washed in the presence of different concentrations of peptide, were expressed as ΔE, calculated from the following equation:

$$(\Delta E) = \sqrt{(\Delta L)^2 + (\Delta a)^2 + (\Delta b)^2}$$

The whiteness (ΔL) and the colour difference (ΔE) obtained by the above method are given in the following Table.

| | Peptide | | Tyrosine | |
|---|---|---|---|---|
| Concentration | ΔL | ΔE | ΔL | ΔE |
| 25 μM | 2.40 | 2.46 | −0.5 | 0.55 |
| 50 μM | 2.80 | 2.85 | −0.6 | 0.63 |
| 100 μM | 3.50 | 3.62 | −2.0 | 2.05 |

The addition of the peptide enhancer results in a clear dye transfer prevention benefit, resulting in a lighter white swatch. The use of free tyrosine even results n darkening of the white swatch (negative ΔL).

What is claimed is:

1. An enzymatic oxidation process wherein a substance which is to be oxidized is reacted with (a) an enzyme exhibiting peroxidase activity and a source of hydrogen peroxide or an enzyme exhibiting oxidase activity on phenolic compounds and (b) a peptide which enhances the oxidation activity of the enzyme) characterized in that the compound selectively binds the substance which is to be oxidized and the substance which is to be oxidized is selected from the group consisting of porphyrin derived structures, tannins, polyphenols, carotenoids, anthocyanins, maillard reaction products and textile dyes.

2. Process according to claim 1, wherein the peptide contains one or more tyrosine residues.

3. Process according to claim 1, wherein the binding compound has a chemical equilibrium constant $K_d$ for the substance of less than $1*10^{31\ 4}$.

4. Process according to claim 1, wherein the chemical equilibrium constant $K_d$ for the substance is less than $1*10^{-7}$.

5. Process according to claim 3, wherein the binding compound has a chemical equilibrium constant $K_d$ for the substance of less than $1*10^{31\ 6}$.

* * * * *